US010401367B2

(12) United States Patent
Yoon

(10) Patent No.: US 10,401,367 B2
(45) Date of Patent: Sep. 3, 2019

(54) METHOD AND APPARATUS FOR ANALYZING PROTEIN-PROTEIN INTERACTION ON SINGLE MOLECULE LEVEL WITHIN THE CELLULAR ENVIRONMENT

(71) Applicant: KOREA ADVANCED INSTITUTE OF SCIENCE AND TECHNOLOGY, Daejeon (KR)

(72) Inventor: Tae-Young Yoon, Daejeon (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 0 days.

(21) Appl. No.: 15/945,890

(22) Filed: Apr. 5, 2018

(65) Prior Publication Data
US 2018/0284127 A1    Oct. 4, 2018

Related U.S. Application Data

(60) Division of application No. 15/642,427, filed on Jul. 6, 2017, now Pat. No. 9,964,544, which is a division of application No. 15/211,096, filed on Jul. 15, 2016, now Pat. No. 9,733,255, which is a division of application No. 14/059,349, filed on Oct. 21, 2013, now Pat. No. 9,423,400, which is a continuation of application No. PCT/KR2012/003077, filed on Apr. 20, 2012.

(30) Foreign Application Priority Data

Apr. 20, 2011   (KR) .................. 10-2011-0036942
Aug. 31, 2011   (KR) .................. 10-2011-0088062
Aug. 31, 2011   (KR) .................. 10-2011-0088084

(51) Int. Cl.
| | | |
|---|---|---|
| *G01N 31/00* | (2006.01) | |
| *G01N 33/53* | (2006.01) | |
| *G01N 33/68* | (2006.01) | |
| *G01N 21/64* | (2006.01) | |
| *G01N 33/574* | (2006.01) | |
| *G01N 21/77* | (2006.01) | |

(52) U.S. Cl.
CPC ..... *G01N 33/6845* (2013.01); *G01N 21/6428* (2013.01); *G01N 21/6486* (2013.01); *G01N 21/77* (2013.01); *G01N 33/574* (2013.01); *G01N 21/648* (2013.01); *G01N 21/6458* (2013.01); *G01N 2021/7786* (2013.01)

(58) Field of Classification Search
None
See application file for complete search history.

(56) References Cited

U.S. PATENT DOCUMENTS

| | | | | |
|---|---|---|---|---|
| 9,377,462 | B2* | 6/2016 | Yoon | G01N 33/6845 |
| 9,423,400 | B2* | 8/2016 | Yoon | G01N 33/6845 |
| 9,733,255 | B2* | 8/2017 | Yoon | G01N 33/6845 |
| 9,739,785 | B2* | 8/2017 | Yoon | G01N 33/6845 |
| 9,964,544 | B2* | 5/2018 | Yoon | G01N 33/6845 |
| 2003/0186311 | A1 | 10/2003 | Henderson et al. | |
| 2003/0224459 | A1 | 12/2003 | Yasukawa et al. | |
| 2007/0105157 | A1 | 5/2007 | Liotta | |
| 2007/0128665 | A1 | 6/2007 | Lockyer | |
| 2010/0330698 | A1 | 12/2010 | Evers | |
| 2011/0086779 | A1 | 4/2011 | Wagner et al. | |

FOREIGN PATENT DOCUMENTS

| | | |
|---|---|---|
| CN | 1527720 | 9/2004 |
| CN | 1732387 | 2/2006 |
| CN | 101105493 | 1/2008 |
| CN | 101124472 | 2/2008 |
| CN | 101303354 | 11/2008 |
| CN | 101443460 | 5/2009 |
| JP | 09-222428 | 8/1997 |
| JP | 2000516706 | 12/2000 |
| JP | 2001103867 | 4/2001 |
| JP | 2001242116 | 9/2001 |

(Continued)

OTHER PUBLICATIONS

Kodadek, Thomas, "Protein microarrays: prospects and problems", Chemistry & Biology, Issue 8, Feb. 2001, 105-115.

(Continued)

*Primary Examiner* — Lisa V Cook
(74) *Attorney, Agent, or Firm* — Lex IP Meister, PLLC

(57) ABSTRACT

A method of analyzing protein-protein interactions includes binding the first proteins to the substrate where the first proteins are tagged with the first markers which bind specifically to the biomolecules immobilized on the substrate or the first proteins bind specifically to the biomolecules immobilized on the substrate; incubating the substrate bound first proteins with cell lysate containing the second proteins which are tagged with second markers; analyzing the interactions between the first proteins and the second proteins in the cell lysate, and obtaining the first analytic value representing the kinetic picture of the interactions; incubating the substrate bound first proteins with cell lysate mixture of a cell lysate consisting of the second markers-tagged second proteins and another cell lysate comprising other proteins including unlabelled second proteins and obtaining the second analytic value; comparing and analyzing the first and the second analytic values.

9 Claims, 7 Drawing Sheets

(56) References Cited

FOREIGN PATENT DOCUMENTS

| | | |
|---|---|---|
| JP | 2002-253240 | 9/2002 |
| JP | 2003-294631 | 10/2003 |
| JP | 2004-012176 | 1/2004 |
| JP | 2005-257274 | 9/2005 |
| JP | 2008082715 | 4/2008 |
| JP | 2008-190879 | 8/2008 |
| JP | 2014514569 | 6/2014 |
| JP | 5903486 | 4/2016 |
| KR | 10-0741160 | 7/2007 |
| KR | 10-0845139 | 7/2008 |
| KR | 10-0886312 | 3/2009 |
| KR | 10-0908641 | 7/2009 |
| KR | 10-2010-0012714 | 2/2010 |
| WO | 2005085801 | 9/2005 |
| WO | 2006107864 | 10/2006 |
| WO | 2009100442 | 8/2009 |
| WO | 2010114031 | 10/2010 |
| WO | 2010123608 | 10/2010 |
| WO | 2011-007138 | 1/2011 |

OTHER PUBLICATIONS

Lleres, D. et al, "Detecting Protein-Protein Interactions In Vivo with FRET using Multiphoton Fluorescence Lifetime Imaging Microscopy (FUM)", Current Protocols in Cy10metry 12.10.1-12.10.19, Oct. 2007.

Lee et al., "Real-time single-molecule co-immunoprecipitation analyses reveal cancer-specific Ras signalling dynamics," Nature Communications, published Feb. 19, 2013, pp. 1-9.

Lee et al., "Real-time single-molecule coimmunoprecipitation of weak protein-protein interactions," Nature America, Inc., Nature Protocols, vol. 8, No. 10, Sep. 26, 2013, pp. 2045-2060.

Nagy et al., "Activation-dependent clustering of the erbB2 receptor tyrosine kinase detected by scanning near-field optical microscopy," The Company of Biologist Limited, Journal of Cell Science, 112, May 11, 1999, pp. 1733-1741.

Roy et al., "A practical guide to single-molecule FRET," Nature Publishing Group, Nature Methods, vol. 5, No. 6, Jun. 2008, pp. 508-516.

Sako et al., "Single-molecule imaging of EGFR signalling on the surface of living cells," Nature Cell Biology, vol. 2, Mar. 2000, pp. 168-172.

Wabuyele et al., "Near-Field Scanning Optical Microscopy for Bioanalysis at Nanometer Resolution," Methods in Molecular Biology, vol. 300: Protein Nanotechnology, Protocols, Instrumentation, and Applications, Dec. 2, 2005, pp. 437-452.

Javaherian et al., "Selection of aptamers for a protein target in cell lysate and their application to protein purification", Nucleic Acids Research, Mar. 20, 2009, Vol.37, No. 8, e62, pp. 1-10.

Petricoin et al., "Clinical Proteomics: Translating Benchside Promise Into Bedside Reality", Nature Reviews, Drug Discovery, vol. 1, Sep. 2002, pp. 683-695.

Notice of Allowance, Japan Patent Office, dated Feb. 16, 2016, Patent Application No. 2014-506337.

* cited by examiner

US 10,401,367 B2

METHOD AND APPARATUS FOR ANALYZING PROTEIN-PROTEIN INTERACTION ON SINGLE MOLECULE LEVEL WITHIN THE CELLULAR ENVIRONMENT

CROSS-REFERENCE TO RELATED APPLICATIONS

This application is a Divisional application of U.S. patent application Ser. No. 15/642,427 filed on Jul. 6, 2017 (now U.S. Pat. No. 9,964,544), which is a Divisional Application of U.S. patent application Ser. No. 15/211,096 filed on Jul. 15, 2016 (now U.S. Pat. No. 9,733,255), which is a Divisional Application of U.S. U.S. patent application Ser. No. 14/059,349 filed on Oct. 21, 2013 (now U.S. Pat. No. 9,423,400) and claims the benefit of U.S. patent application Ser. No. 14/059,294 (now U.S. Pat. No. 9,377,462), which is a continuation of International Application No. PCT/KR2012/003077 filed on Apr. 20, 2012, which claims priority to Korean Patent Application No. 10-2011-0036942 filed on Apr. 20, 2011, Korean Patent Application No. 10-2011-0088062 filed on Aug. 31, 2011, and Korean Patent Application No. 10-2011-0088084 filed on Aug. 31, 2011, which are incorporated herein by reference.

TECHNICAL FIELD

The present invention relates to a method of analyzing protein-protein interactions. More specifically, the present invention relates to a method and an apparatus for analyzing protein-protein interactions at the single molecule level in the context of their normal intracellular environment, as well as the degree of the effects of different proteins on a specific protein-protein interaction in the context of the actual intracellular environment.

BACKGROUND ART

A cell maintains a life phenomenon by performing a variety of biological functions, such as gene expression, cell growth, cell cycle, metabolism, signal transduction, and the like, which are mediated by various and complex protein-protein interactions. Accordingly, understanding the nature and function of such intracellular protein-protein interactions has been a major foundation of our understandings of basic cellular processes, and has also played an essential part in our ability to develop new drugs and treat diseases.

A representative method of investigating protein-protein interactions in vitro is an affinity chromatography method.

In the case of protein affinity chromatography, protein has to go through demanding and complex purifying processes. Disadvantageously, since the interactions between proteins are only assessed in vitro, this methodology may result in false-positive results. For example, proteins can be bound by an electrostatic interaction while they pass through a column.

In order to perform a quantitative measurement, a method of investigating the protein-protein interactions according to conventional art technologies analyzes the interactions in the isolation. In other words, the interaction of proteins of interest is assessed in the absence of other intracellular materials by isolating and purifying each of the proteins away from the cellular milieu and analyzing the protein-protein interactions. Disadvantageously, these conventional art technologies limit, or prevent, the ability to analyze the protein-protein interactions at the single molecular level in the context of the normal intracellular environment (e.g., in the presence of other proteins, and the like).

Moreover, methods of investigating protein-protein interactions according to the conventional technologies are also disadvantageous because they do not allow assessment of the degrees of effects that other proteins may have on specific protein-protein interactions in the context of the actual intracellular environment.

SUMMARY OF THE DISCLOSURE

An object of the present invention is to provide a method and an apparatus for analyzing protein-protein interactions, which can analyze the protein-protein interactions at a single molecule level in the context of the normal intracellular environment. Additionally, an object of the invention is to also assess the degree of effects of different proteins on specific protein-protein interactions when the different proteins are present in the normal intracellular environment.

Accordingly, an exemplary embodiment of the present invention provides a method of analyzing interactions between first proteins and second proteins at a single molecule level, comprising: (a) binding the first proteins to the substrate where the first proteins are tagged with the first markers which bind specifically to the biomolecules immobilized on the substrate; (b) incubating the substrate bound first proteins with cell lysate containing the second proteins which are tagged with second markers; and (c) analyzing the interactions between the first proteins and the second proteins in the cell lysate.

According to another aspect of the present invention, there is provided a method of analyzing interactions between first proteins and second proteins at a single molecular level, comprising: (a) binding the first proteins to the substrate where first proteins bind specifically to the biomolecules immobilized on the substrate; (b) incubating the substrate bound first proteins with cell lysate containing the second proteins which are tagged with second markers; and (c) analyzing the interactions between the first proteins and the second proteins in the cell lysate.

According to a preferred embodiment, step (c) includes measuring a fluorescent signal having a specific wavelength generated by the markers included in the second proteins bound to the first proteins using an optical apparatus generating a near-field. Preferably, in the step (c), the fluorescent signal having the specific wavelength is cumulatively measured for a predetermined time period. Preferably, in the step (c), the fluorescent signal having the specific wavelength is measured in real time under the presence of the cell lysate supplied to the substrate.

Preferably, the step (a) includes supplying the cell lysate comprising the first proteins.

Preferably, the method further comprises supplying a buffer solution to the substrate before the step (b).

Preferably, the first markers and the second markers are fluorescent proteins having different wavelengths.

According to yet another aspect of the present invention, there is provided a method of analyzing interactions between first proteins and second proteins at a single molecular level, comprising: (a) binding the first proteins to the substrate where the first proteins are tagged with the first markers that bind specifically to the biomolecules immobilized on the substrate; (b) incubating the substrate bound first proteins with cell lysate containing the second proteins which are tagged with the second markers; (c) analyzing the interactions between the first proteins and the second proteins in the cell lysate, and obtaining the first analytic value representing the kinetic picture of the interactions; (d) incubating the substrate bound first proteins from step (a) with a cell lysate mixture of a cell lysate from the step (b) and another cell lysate having other proteins; (e) and analyzing the interactions between the first proteins and the second proteins in the presence of other proteins from the cell lysate mixture, and obtaining the second analytic value representing the kinetic picture of the interactions; and (f) comparing and analyzing the first and the second analytic values.

According to still another aspect of the present invention, there is provided a method of analyzing interactions between first proteins and second proteins at a single molecular level, comprising: (a) binding the first proteins to the substrate where the first proteins bind specifically to the biomolecules which are immobilized on the substrate; (b) incubating the substrate bound first proteins with cell lysate containing the second proteins which are tagged with the second markers; (c) analyzing the interactions between the first proteins and the second proteins in the cell lysate, and obtaining the first analytic value representing the kinetic picture of the interactions; (d) incubating the substrate bound first proteins from step (a) with a cell lysate mixture of a cell lysate from the step (b) and another cell lysate having other proteins; (e) and analyzing the interactions between the first proteins and the second proteins in the presence of other proteins from the cell lysate mixture, and obtaining the second analytic value representing the kinetic picture of the interactions; and (f) comparing and analyzing the first and the second analytic values.

Preferably, the step (c) includes measuring a fluorescent signal having a specific wavelength generated by the second markers tagged on second proteins when they are bound to the first proteins. Here, an optical apparatus generating a near-field is used.

Preferably, in the step (c), the fluorescent signal having the specific wavelength is cumulatively measured for a predetermined time period.

Preferably, in the step (c), the fluorescent signal having the specific wavelength is measured in real time under the presence of the cell lysate supplied to the substrate.

Preferably, the step (a) includes supplying the cell lysate comprising the first proteins.

Preferably, the method further comprises supplying a buffer solution to the substrate before the step (b).

Preferably, the first markers and the second markers are fluorescent proteins having different wavelengths.

According to yet still another aspect of the present invention, there is provided an apparatus of analyzing interactions between first proteins and second proteins at a single molecular level, comprising: a sample loading unit for loading a substrate comprising attached biomolecules which specifically bind to first markers tagged on the first proteins, wherein the first proteins are supplied to the substrate to induce binding of the biomolecules and the first markers, and cell lysate containing the second markers-tagged second proteins are supplied to the substrate; an optical excitation unit for generating a near-field having a first wavelength to a surface of the substrate loaded on the sample loading unit; and an optical measuring unit for detecting a change from the first wavelength to a second wavelength on the surface of the substrate according to the interactions between the first proteins and the second proteins in the cell lysate.

According to yet still another aspect of the present invention, there is provided an apparatus of analyzing interactions between first proteins and second proteins at a single molecular level, comprising: a sample loading unit for loading a substrate comprising attached biomolecules which specifically bind to the first proteins, wherein the first proteins are supplied to the substrate and binds to the biomolecules, and cell lysate containing the second markers-tagged second proteins are supplied to the substrate; an optical excitation unit for generating a near-field having a first wavelength to a surface of the substrate loaded on the sample loading unit; and an optical measuring unit for detecting a change from the first wavelength to a second wavelength on the surface of the substrate according to the interactions between the first proteins and the second proteins in the cell lysate.

According to a preferred embodiment, the optical measuring unit cumulatively measures a fluorescent signal having the second wavelength for a predetermined time period.

Preferably, the optical measuring unit measures a fluorescent signal having the second wavelength in real time under the presence of the cell lysate.

Preferably, the first markers and the second markers are fluorescent proteins having different wavelengths.

Preferably, the apparatus further comprises a signal analyzing unit for analyzing the fluorescent signal having the second wavelength measured by the optical measuring unit through image processing.

According to yet still another aspect of the present invention, there is provided an apparatus of analyzing interactions between first proteins and second proteins at a single molecular level, comprising: a sample loading unit for loading a substrate comprising attached biomolecules which specifically bind to first markers tagged on the first proteins, wherein the first proteins are supplied to the substrate to induce binding of the biomolecules and the first markers, and cell lysate containing the second markers-tagged second proteins are supplied to the substrate; an optical excitation unit for generating a near-field having a first wavelength to a surface of the substrate loaded on the sample loading unit; an optical measuring unit for detecting a change from the first wavelength to a second wavelength on the surface of the substrate according to the interactions between the first proteins and the second proteins in the cell lysate; and a signal analyzing unit for obtaining the first analytic value representing the kinetic picture of the interactions by analyzing a fluorescent signal having the second wavelength measured by the optical measuring unit through image processing; wherein a new substrate comprising attached biomolecules which specifically bind to first markers tagged on the first proteins is loaded on the sample loading unit, and cell lysate mixture of a cell lysate consisting of the second markers-tagged second proteins and another cell lysate having other proteins are supplied to the new substrate, such that the optical measuring unit detects a change from the first wavelength to the second wavelength on the surface of the substrate according to interactions between the first proteins and the second proteins in the supply of the cell lysate mixture to the new substrate, and the signal analyzing unit obtains a second analytic value by analyzing a fluorescent signal having the second wavelength measured by the optical measuring unit through image processing.

According to yet still another aspect of the present invention, there is provided an apparatus of analyzing interactions between first proteins and second proteins at a single molecular level, comprising: a sample loading unit for loading a substrate comprising attached biomolecules which specifically bind to the first proteins, wherein the first proteins are supplied to the substrate and binds to the biomolecules, and cell lysate containing the second markers-tagged second proteins are supplied to the substrate; an optical excitation unit for generating a near-field having a first wavelength to a surface of the substrate loaded on the sample loading unit; an optical measuring unit for detecting a change from the first wavelength to a second wavelength on the surface of the substrate according to the interactions between the first proteins and the second proteins in the cell lysate; and a signal analyzing unit obtains a second analytic value by analyzing a fluorescent signal having the second wavelength measured by the optical measuring unit through image processing; wherein a new substrate comprising attached biomolecules which specifically bind to first markers tagged on the first proteins is loaded on the sample loading unit, and cell lysate mixture of a cell lysate consisting of the second markers-tagged second proteins and another cell lysate having other proteins are supplied to the new substrate, such that the optical measuring unit detects a change from the first wavelength to the second wavelength on the surface of the substrate according to interactions between the first proteins and the second proteins in the supply of the cell lysate mixture to the new substrate, and the signal analyzing unit obtains a second analytic value by analyzing a fluorescent signal having the second wavelength measured by the optical measuring unit through image processing.

According to a preferred embodiment, the apparatus further comprising a signal diagnosing unit for comparing and analyzing the first analytic value and the second analytic value.

Preferably, the optical measuring unit cumulatively measures the fluorescent signal having the second wavelength for a predetermined time period.

Preferably, the optical measuring unit measures in real time under the presence of the cell lysate supplied to the substrate.

Preferably, the first marker and the second marker are fluorescent proteins having different wavelengths.

According to the present invention, it is possible to analyze protein-protein interactions at the single molecule level in the context of their normal intracellular environment, as well as the degree of the effects of different proteins on a specific protein-protein interaction in the context of the actual intracellular environment.

BRIEF DESCRIPTION OF DRAWINGS

The above and other objects, features and advantages of the present invention will become more apparent to those of ordinary skill in the art by describing in detail exemplary embodiments thereof with reference to the attached drawings, in which.

DETAILED DESCRIPTION

Hereinafter, exemplary embodiments of the present invention will be described in detail. However, the present invention is not limited to the embodiments disclosed below, but can be implemented in various forms. The following embodiments are described in order to enable those of ordinary skill in the art to embody and practice the present invention.

With reference to the appended drawings, exemplary embodiments of the present invention will be described in detail below. To aid in understanding the present invention, like numbers refer to like elements throughout the description of the figures, and the description of the same elements will be not reiterated.

Figure 1:
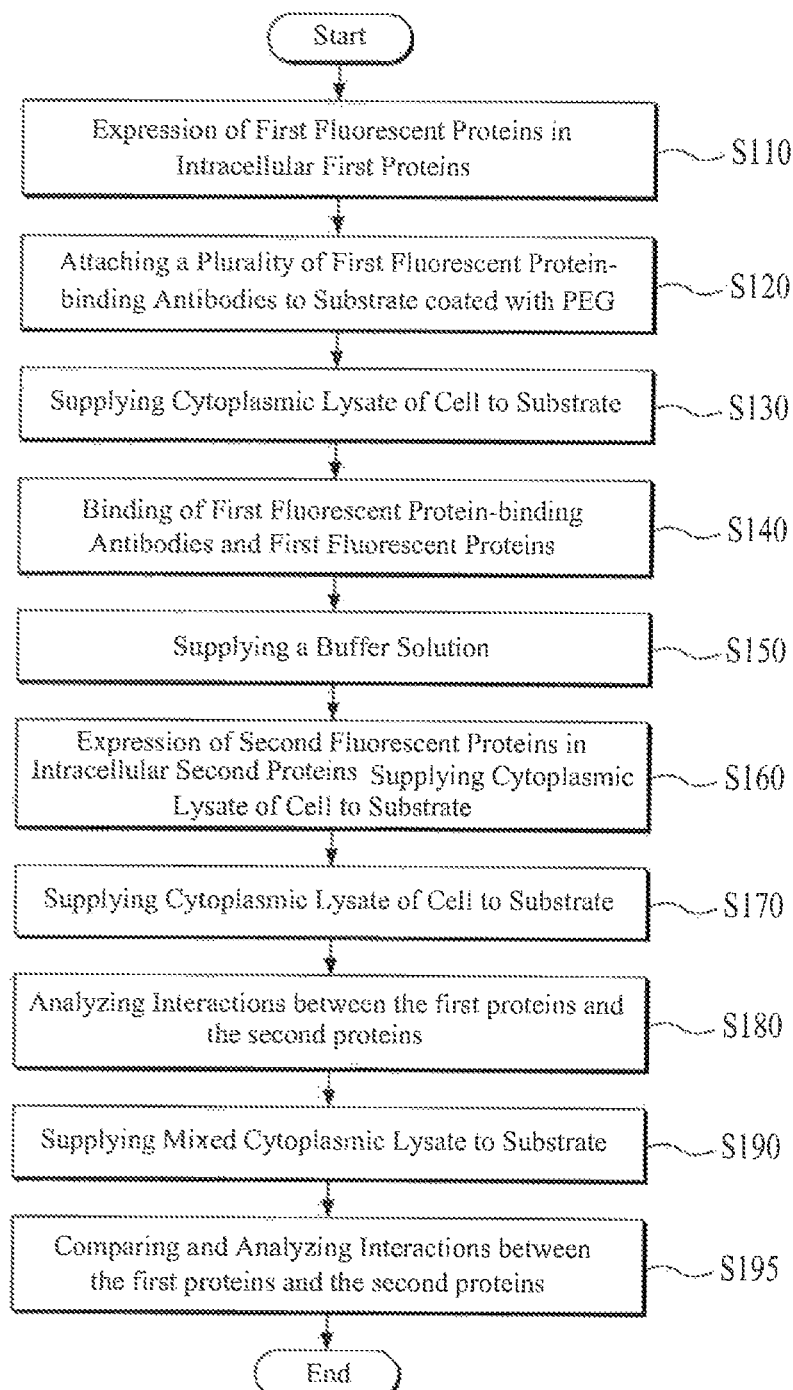
FIG. 1 is a flowchart illustrating a procedure of a method of analyzing protein-protein interactions according to an exemplary embodiment of the present invention.

FIG. 1 is a flowchart illustrating a method of analyzing protein-protein interactions according to an exemplary embodiment of the present invention. Referring to FIG. 1, an analyst performs an expression of first fluorescent protein tags, a marker of first proteins, on the first proteins (i.e. a first protein having a first marker) in relevant cells through genetic manipulation, in order to analyze the interaction between first proteins and second proteins at the single molecule level (S110). According to an exemplary embodiment of the present invention, the first fluorescent proteins may be attached or connected to the first proteins by a physical-chemical method.

According to an exemplary embodiment of the present invention, the first proteins are h-Ras proteins, the second proteins are Ras-binding domain (RBD) proteins of C-Raf, and the first fluorescent proteins are m-Cherry proteins.

Figure 2:
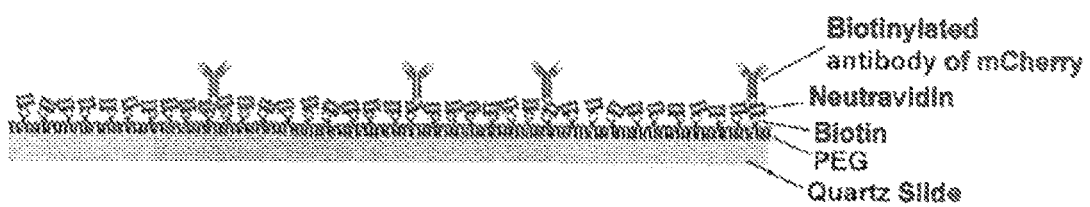
FIG. 2 to FIG. 4 are diagrams illustrating each step of a method of analyzing the protein-protein interactions according to an exemplary embodiment of the present invention.

Subsequently, the analyst attaches first fluorescent protein-binding antibodies that are to be bound to the first fluorescent proteins tagged as the markers to the first proteins in the above-described step, S110, to a substrate that is a quartz slide coated with polyethylene glycol (PEG), as described in FIG. 2 (S120).

According to an exemplary embodiment of the present invention, biomolecules binding to the first fluorescent proteins, such as DNA, RNA, liposome having specific components to be bound to proteins, and the like, may also be used in addition to the antibodies as alternatives.

The analyst then induces (S140) a binding of the first fluorescent protein-binding antibodies and the first fluorescent protein tags, the first markers, on first proteins by supplying (S130) a cytoplasmic lysate of the cell, in which the first fluorescent proteins are tagged to the first proteins, prepared in the above-described step, S110, to the substrate (S140).

Meanwhile, according to the above-described step, S130, cell lysate, for example, cytolysate, diluted cytoplasmic lysate, diluted cytolysate, and the like, may be used in addition to the cytoplasmic lysate.

Figure 3:
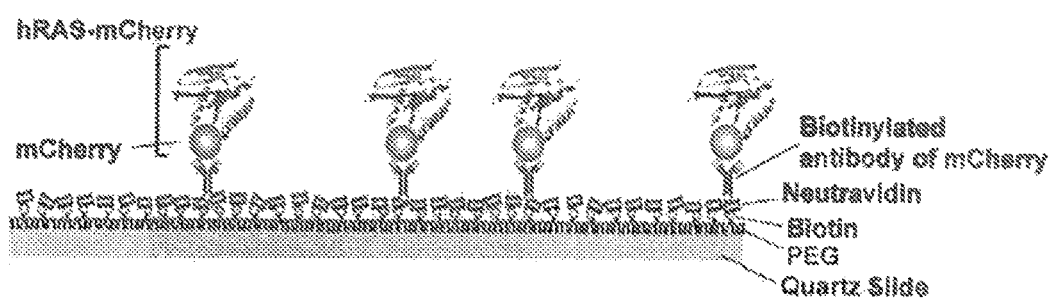

As shown in FIG. 3, the analyst can confirm whether the first fluorescent proteins are bound to a plurality of the first fluorescent protein-binding antibodies attached on the substrate from a change the wavelength emitted by the first fluorescent proteins (i.e., measuring individual single molecular signals generated from the first fluorescent proteins) by performing an observation of a substrate surface using a total internal reflection fluorescence microscope when the first fluorescent proteins are bound to the first fluorescent protein-binding antibodies attached on the substrate.

According to an exemplary embodiment of the present invention, the protein tags, the first markers, on first proteins which bind to the antibodies are not always certain to be fluorescent proteins, but the protein tags on first proteins may be preferably the fluorescent proteins because, when they are not the fluorescent proteins, it cannot be confirmed whether or not they are bound to antibodies through the total internal reflection fluorescence microscope.

In other words, the predetermined protein tags on the first proteins, the first markers, according to the present invention, function as antigens to be bound to the antibodies attached on the substrate. Therefore, the first markers, the predetermined antigens, attached to the first proteins as described above are not always required even to be proteins, but they may also be compounds which are bound to antibodies.

That is, since when the protein tags on the first proteins are the fluorescent proteins, whether they are bound to antibodies or not can be confirmed with the total internal reflection fluorescence microscope, and thus the number of the fluorescent proteins bound to the antibodies attached on the substrate and binding density thereof can be accurately measured.

Once the first fluorescent proteins are bound to a plurality of first fluorescent protein-binding antibodies attached to the substrate, respectively, the analyst removes the remaining materials included in the cytoplasmic lysate except the first proteins tagged with first fluorescent proteins from the substrate by supplying a buffer solution to the substrate (S150).

Subsequently, the analyst performs an expression of second fluorescent protein tags, a marker of the second proteins, on the second proteins (i.e. second proteins having second marker) in relevant cells that are the same type as the cells used in the above-described step, S110 (S160) through genetic manipulation of the second proteins. According to an embodiment of the present invention, the second fluorescent proteins may be attached or connected to the second proteins by a physical-chemical method. In a preferred embodiment of the invention, the second marker emits fluorescence at a different wavelength than the first marker.

The above-described step, S160, may be performed in advance along with the above-described step, S110, in order to smoothly continue the analysis. According to an exemplary embodiment of the present invention, since the second fluorescent proteins preferably have a wavelength range different from the first fluorescent proteins, when the first fluorescent proteins are m-Cherry proteins, the second fluorescent proteins may be chosen as enhanced Green Fluorescent Protein (eGFP) that is a green fluorescent protein.

The analyst supplies the whole cytoplasmic lysate of the cell with the expressed second fluorescent proteins tags on the second proteins in the above-described step, S160, to the substrate (S170).

The above-described step, S170, cell lysate, such as cytolysate, diluted cytoplasmic lysate, diluted cytolysate, and the like, may be used in addition to the cytoplasmic lysate.

The first proteins are bound to a plurality of first fluorescent protein-binding antibodies attached to the surface of the substrate through the first fluorescent proteins, respectively. When the whole cytoplasmic lysate including the second proteins is supplied to the surface of the substrate as mentioned above, the first proteins on the surface of the substrate interact with the second proteins under the same conditions as the intracellular environment, which allows for the coexistence of the second proteins included in the cytoplasmic lysate with native proteins in whole cell lysate.

Figure 4:
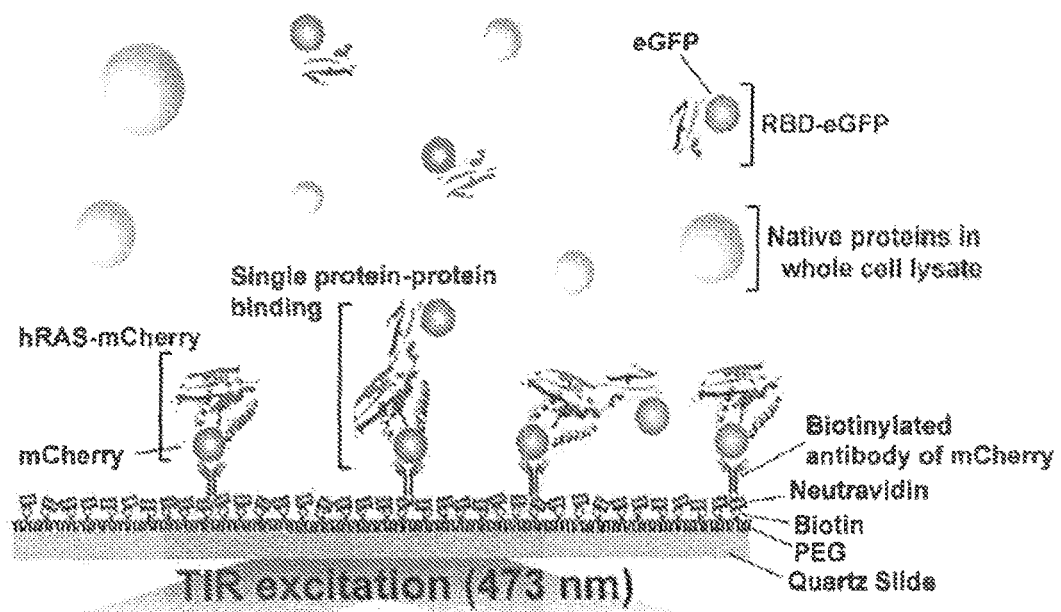

More specifically, as shown in FIG. 4, each of the first proteins bound to each of the antibodies attached on the surface of the substrate through the first fluorescent proteins may bind and unbind with the second protein repeatedly at the single molecule level under the same conditions as the intracellular environment to repeat the binding and unbinding.

As shown in FIG. 4, when binding occurs between the first proteins and the second proteins at the single molecule level, the analyst can confirm that the wavelength at the surface of the substrate is changed from 473 nm to 520 nm by eGFP, e.g. the second fluorescent protein tags on the second proteins by observing the surface of the substrate through an optical apparatus that can generate a near-field, such as the total internal reflection fluorescence microscope having a wavelength of 473 nm.

In other words, the binding/unbinding state between the first proteins and the second proteins can be confirmed by a detection of fluorescence signals of a specific wavelength bandwidth (520 nm) generated from the second fluorescent proteins (eGFP) near the surface of the substrate through the binding between the first proteins and the second proteins, and the analyst can analyze the interactions, such as the frequencies of the binding and unbinding between the first proteins and the second proteins, and the like, at the single molecule level by continuously observing the change of wavelength at each of binding/unbinding positions on the substrate (S180).

In addition, the interaction, such as the frequencies of the binding and unbinding between the first proteins and the second proteins, and the like, can be analyzed in an environment equivalent to the normal intracellular by measuring the fluorescence signals having a specific wavelength in real time under the presence of the cytoplasmic lysate supplied to the substrate in the above-described step, S170.

It is possible that the second proteins that are not bound to the first proteins may be moved closer to the surface of the substrate in the process of floating and moving in the cytoplasmic lysate supplied to the substrate. Consequently, this may introduce errors into the analysis of the protein-protein interactions caused by changing the wavelength from 473 nm to 520 nm on the surface of the substrate by eGFP, i.e., the second fluorescent protein tags on second proteins when observing the surface through the total internal reflection fluorescence microscope.

Therefore, according to an embodiment of the present invention, when the change of wavelength is measured on the surface of the substrate through the total internal reflection fluorescence microscope, the change of wavelength may be preferably cumulatively measured for a predetermined time period.

Since the rate of the movement of the second proteins that are not bound to the first proteins floating in the cytoplasmic lysate are very fast, although the second proteins temporarily move near the surface of the substrate during floating and moving, they leave the surface of the substrate again during the time of cumulatively measuring.

To verify this, it was experimentally confirmed that the wavelength is not changed when change of wavelength is cumulatively measured on the surface of the substrate in an integral section of, for example, 50 msec. Here, all of the second proteins in the cytoplasmic lysate were floating and moving without binding to the first proteins by, for example, mutating proteins not to bind each others.

According to an exemplary embodiment of the present invention, the value of analyzing protein-protein interactions in the above-described step, S180, is secured as a first analytic value and the value of analyzing protein-protein interactions in the following different environment is secured as a second analytic value, which allows the comparative analysis of both values.

That is, the analyst repeats equally S110 to S160 as described above after securing the value of analyzing the interaction in the above-described step, S180, as the first analytic value.

In order to perform the above-described step, S170, the analyst supplies a mixture of s cytoplasmic lysate and the cytoplasmic lysate from, for example, a tumor cell, the like, and the cytoplasmic lysate of the relevant cell which does not contain the second fluorescent proteins-tagged second proteins in the above-described step, S160, to the substrate (S190).

In order to perform the above-described step, S190, mixed cell lysate, such as mixed cytolysate, diluted mixed cytoplasmic lysate, diluted mixed cytolysate, and the like, may be used in addition to the mixed cytoplasmic lysate.

The first proteins are bound to a plurality of first fluorescent protein-binding antibodies attached on the surface of the substrate through the first fluorescent proteins, respectively. When the mixture of a cytoplasmic lysate of interest and the cytoplasmic lysate including the second proteins is supplied to the surface of the substrate, this allows the first proteins on the surface of the substrate to interact not only with second fluorescence protein tagged second proteins in the cytoplamic lysate but also with coexisting unlabeled second proteins and native proteins in the whole cell lysate.

In other words, unlike the above-described step, S180, the second proteins tagged with second fluorescent proteins interact with the first proteins on the surface of the substrate in competition with coexisting second proteins without second fluorescent proteins tag in the cell lysate of interest. Moreover, the interactions of the second fluorescent proteins tagged second proteins with the first proteins are affected by other proteins in the cell of interest.

The degrees of effects caused by the second proteins in the cells of interest or other proteins in the cells of interest as mentioned above may be confirmed by analyzing the interactions, such as the frequencies of the binding and unbinding of the second proteins-tagged with second fluorescent proteins and the first proteins on the surface of the substrate through an observation of the surface of the substrate using an optical apparatus generating a near-field, such as the total internal reflection fluorescence microscope, and the like, like the above-described step, S180, by the analyst (S195).

More specifically, the analyst can analyze the degrees of effects on promoting or inhibiting the interactions with the second proteins in other cells and other proteins in other cells for the interactions between the second proteins and the first proteins by comparing and analyzing the second analytic value, that is the value for analyzing in the above-described step, S195, and the first analytic value as mentioned above.

Figure 5:
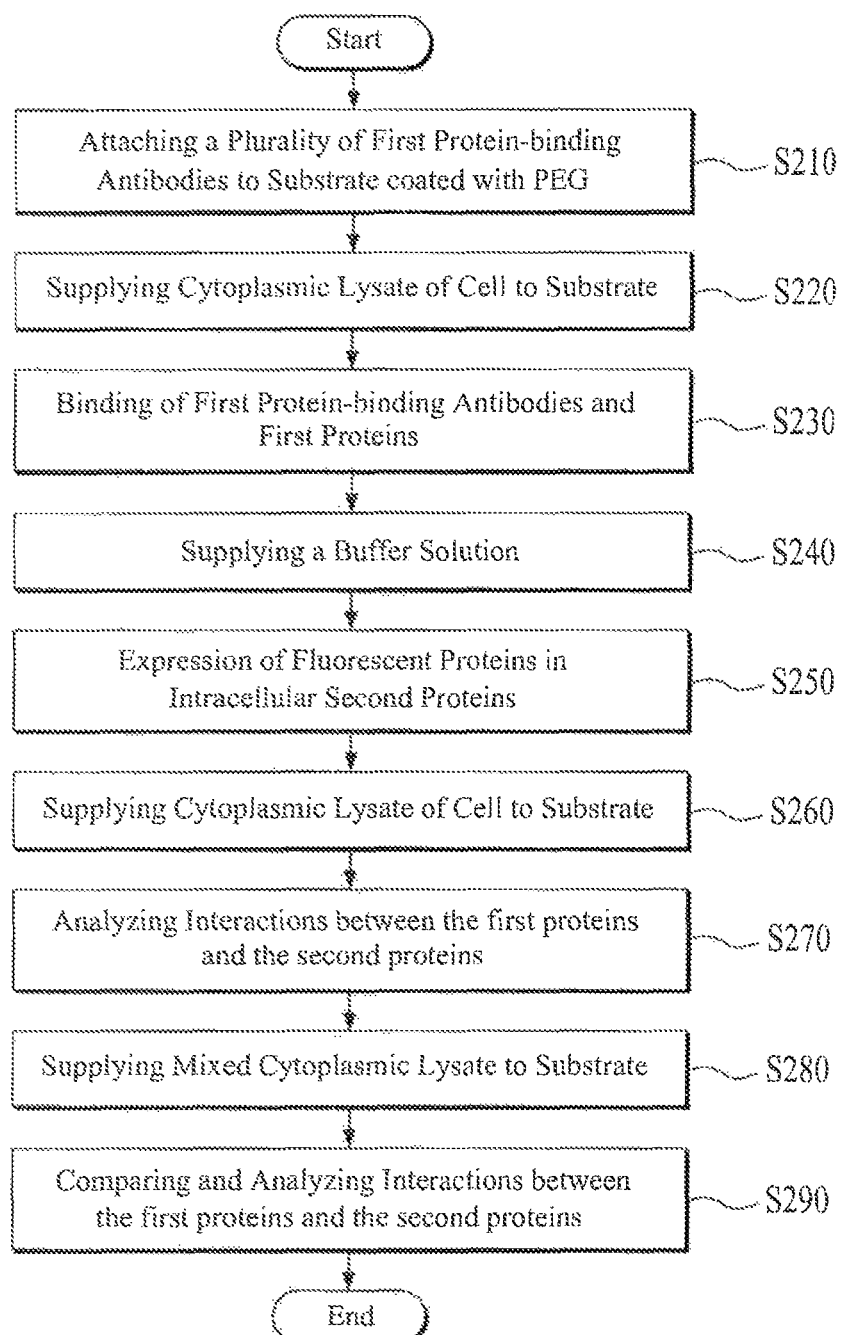
FIG. 5 is a flowchart illustrating a procedure of a method of analyzing the protein-protein interactions according to another exemplary embodiment of the present invention.

FIG. 5 is a flowchart illustrating a procedure of a method of analyzing the protein-protein interactions according to another exemplary embodiment of the present invention. As shown in FIG. 5, the interactions between the first proteins and the second proteins may be analyzed in the direct binding of the first proteins to the antibodies attached to the substrate by attaching the first protein-binding antibodies, not the first fluorescent protein-binding antibodies to the substrate and not expressing the first fluorescent proteins in the first proteins.

Referring to FIG. 5, for the method of analyzing protein-protein interactions according another exemplary embodiment of the present invention, the analyst attaches first fluorescent protein-binding antibodies to be bound to the first proteins to a substrate that is a quartz slide coated with polyethylene glycol (PEG) in order to analyze the interactions between the first proteins and the second proteins that are specific two proteins at the single molecule level (S210).

According to an exemplary embodiment of the present invention, biomolecules binding to the first fluorescent proteins, such as DNA, RNA, liposome having specific components to be bound to proteins, and the like, may also be used in addition to the antibodies as alternatives. Subsequently, the analyst induces the bindings between the first proteins and the first protein-binding antibodies by supplying the cytoplasmic lysate (S220) of the cell including the first proteins to the substrate (S230).

In order to perform the above-described step, S220, cell lysate, such as cytolysate, diluted cytoplasmic lysate, diluted cytolysate, and the like, may be used in addition to the cytoplasmic lysate.

According to another exemplary embodiment of the present invention, the analyst may pre-treat to express the predetermined fluorescent protein tags, such as m-Cherry, on the first proteins. In this case, when the first protein-binding antibodies are bound to the first proteins, the analyst may confirm whether the first proteins are bound to a plurality of the first protein-binding antibodies attached on the substrate from the change of wavelength by the first fluorescent proteins tags on the first proteins through performing an observation of the surface of the substrate using the total internal reflection fluorescence microscope.

Respectively, the analyst removes the remaining materials included in the cytoplasmic lysate except the first proteins from the substrate by supplying a buffer solution to the substrate (S240). Subsequently, the analyst manipulates the cells to express fluorescent protein tagged second proteins through genetic manipulations of second proteins in different cells that are the same type as the above-described cells (S250).

The above described step, S250, may be performed in advance before the above-described step, S210, in order to smoothly continue the analysis. According to an preferred embodiment of the present invention, the fluorescent proteins that are expressed on the second proteins may be eGFP.

Subsequently, the analyst supplies the whole cytoplasmic lysate of the cell having the expressed fluorescent protein tags on second proteins to the substrate (S260).

In order to perform the above-described step, S260, cell lysate, such as cytolysate, diluted cytoplasmic lysate, diluted cytolysate, and the like, may be used in addition to the cytoplasmic lysate.

A plurality of the first protein-binding antibodies attached on the surface of the substrate is bound to the first proteins, respectively. When the whole cytoplasmic lysate including the second proteins is supplied to the surface of the substrate as described above, the first proteins on the surface of the substrate interact with the second proteins included in the cytoplasmic lysate in the same conditions as the intracellular environment.

In other words, each first protein bound to each antibody attached on the surface of the substrate interacts with the second protein in the same conditions as the normal intracellular environment so that as they do in the cell, they are repeatedly bound and unbound at the single molecular level.

When the first proteins are bound to the second proteins at the single molecule level, the wavelength on the surface of the substrate is changed from 473 nm to 520 nm by fluorescent protein tags, i.e., eGFPs, on the second proteins; and the analyst may confirm the bindings state between the first proteins and the second proteins through the above-mentioned change of wavelength by observing the surface of the substrate using the total internal reflection fluorescence microscope and may analyze the interactions, such as the frequencies of the binding and unbinding between the first proteins and the second proteins, and the like, by continuously observing the change of wavelength of each antibody attached to the surface of the substrate (S270).

Moreover, for performing the method of analyzing protein-protein interactions according to another embodiment of the present invention as shown in FIG. 5, the value of analyzing the protein-protein interactions in the above-described step, S270, is secured as a first analytic value and the value of analyzing the protein-protein interactions in the following different environment is secured as a second analytic value, and then both of the values may be compared and analyzed.

In other words, the analyst performs the above-described steps, S210 to S250, equally and repeatedly, after securing the value of analyzing the interactions in the above-described step, S270 as the first analytic value.

In order to perform the above-described step, the analyst supplies a mixture of s cytoplasmic lysate and the cytoplasmic lysate from, for example, a tumor cell, the like, and the cytoplasmic lysate of the relevant cell which does not contain the second fluorescent proteins-tagged second proteins in the above-described step, S260 (S280).

For performing the above-described step, S280, mixed cell lysate, such as mixed cytolysate, diluted mixed cytoplasmic lysate, diluted mixed cytolysate, and the like, may be used in addition to the mixed cytoplasmic lysate.

The first proteins are bound to a plurality of first fluorescent protein-binding antibodies attached on the surface of the substrate through the first fluorescent proteins, respectively. When the mixture of a cytoplasmic lysate of interest and the cytoplasmic lysate including the second proteins is supplied to the surface of the substrate, this allows the first proteins on the surface of the substrate to interact not only with second fluorescence protein tagged second proteins in the cytoplamic lysate but also with coexisting unlabeled second proteins and native proteins in the whole cell lysate.

In other words, unlike the above-described step, S270, the second proteins tagged with second fluorescent proteins interact with the first proteins on the surface of the substrate in competition with coexisting second proteins without second fluorescent proteins tag in the cell lysate of interest. Moreover, the interactions of the second fluorescent proteins tagged second proteins with the first proteins are affected by other proteins in the cell of interest.

The degrees of effects caused by the second proteins in the cells of interest or other proteins in the cells of interest as mentioned above may be confirmed by analyzing the interactions, such as the frequencies of the binding and unbinding of the second proteins-tagged with second fluorescent proteins and the first proteins on the surface of the substrate through an observation of the surface of the substrate using an optical apparatus generating a near-field, such as the total internal reflection fluorescence microscope, and the like, like the above-described step, S180, by the analyst (S290).

More specifically, the analyst may analyze the degrees of effects, for example, enhancement or inhibition effects of other proteins and second proteins inside the other cells to interactions between the second proteins and the first proteins by comparing and analyzing the second analytic value that is the analytic value in the above-described step, S290, and the first analytic value as mentioned above.

Figure 6:
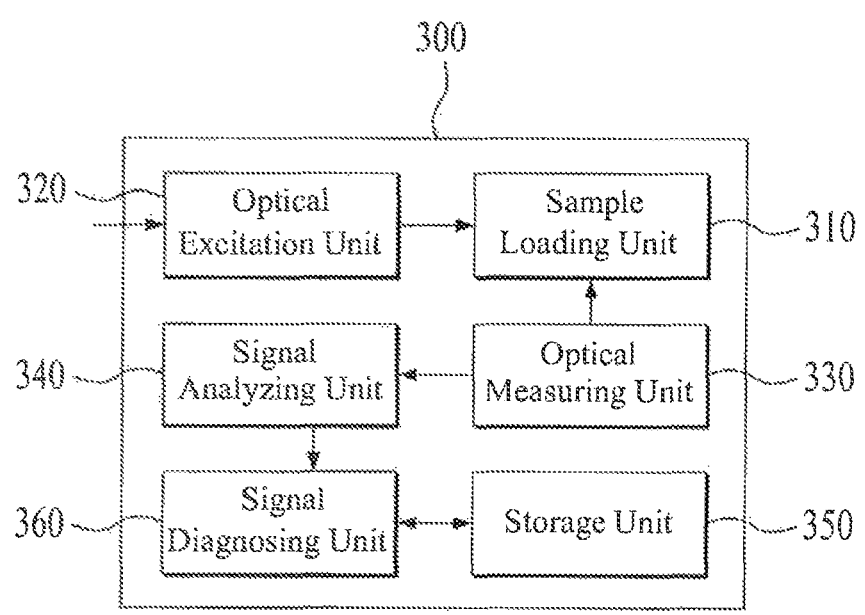
FIG. 6 is a function block diagram showing an exemplary structure of an apparatus performing a method of analyzing the protein-protein interactions in FIG. 1 to FIG. 5.

Meanwhile, a method of analyzing the protein-protein interactions according to the present invention as shown in FIG. 1 to FIG. 5 may be performed in an analysis apparatus having the structure as shown in FIG. 6.

Referring to FIG. 6, the analysis apparatus 300 for analyzing the protein-protein interactions according to an exemplary embodiment of the present invention includes an optical excitation unit 320, a sample loading unit 310, an optical measuring unit 330, a signal analyzing unit 340, a signal diagnosing unit 360, and a storage unit 350.

Firstly, the substrate used for the method of analyzing the protein-protein interactions in the above-described present invention is loaded on the sample loading unit 310. The optical excitation unit 320 generates a near-field having a first wavelength on the surface of the substrate loaded on the sample loading unit 310.

The optical measuring unit 330 detects the change of wavelength from the first wavelength to the second wavelength on the surface of the substrate according to the interactions between the second proteins having the fluorescent proteins and the first proteins attached to the surface of the substrate in the supply of the mixed cytoplasmic lysate or the cytoplasmic lysate to the substrate.

According to an embodiment of the present invention, when the fluorescent proteins having the second proteins are eGFP, the first wavelength would be 473 nm and the second wavelength would be 520 nm.

Moreover, the optical measuring unit 330 may: cumulatively measure the fluorescent signal of the second wavelength for a predetermined time period; also measure the fluorescent signal of the second wavelength in real time under the presence of the cytoplasmic lysate or mixed cytoplasmic lysate on the substrate; and may preferably have single molecular sensitivity for measuring the same.

Meanwhile, the signal analyzing unit 340 analyzes the fluorescent signal of the second wavelength measured by the optical measuring unit 330 through image processing to calculate an analytic value and then stores the calculated analytic value in the storage unit 350.

In addition, the signal analyzing unit 340 analyzes values individually calculated based on the fluorescent signal of the second wavelength as measured by the optical measuring unit 330 in each situation, in which various cytoplasmic lysate, such as the cytoplasmic lysate, mixed cytoplasmic lysate, and the like, are supplied to the substrates. Then the signal analyzing unit 340 stores the values in the storage unit 350.

Figure 7:
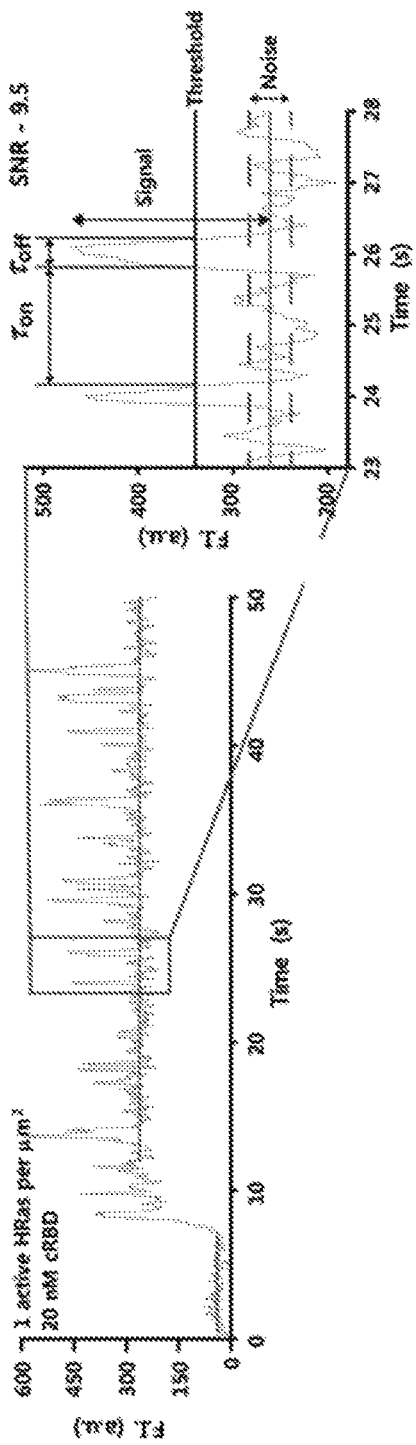
FIG. 7 is a diagram showing a signal measured by an optical measuring unit of the apparatus of analyzing the protein-protein interactions according to an exemplary embodiment of the present invention.

Specifically, the signal analyzing unit 340 finds a baseline of signal marked with a red line among the fluorescent signals measured by the optical measuring unit 330 as shown in FIG. 7.

The baseline of signal is increased between 10 seconds and 20 seconds, which means that the cytoplasmic lysate or mixed cytoplasmic lysate including the second proteins arrives at an imaging region of the optical measuring unit 330.

Meanwhile, the signal analyzing unit 340 measures a fluctuation (e.g., Noise) generated around the increased signal baseline and then sets a threshold that defines the meaningful protein-protein interactions based on the noise.

The noise generated around the signal baseline may be formed by the movements of the second proteins that are continuously, and quickly moved around without interacting with the proteins and the signal analyzing unit 340 sets the baseline as a value that cannot be exceeded by the noise regardless of the above interactions.

When there is a signal that exceeds the baseline, the signal analyzing unit 340 decides that there are meaningful interactions between the first proteins and the second proteins at the relevant point, measures the time ($\tau_{off}$) of the duration of the interactions and the time ($\tau_{on}$) required for forming the following bindings between the first proteins and the second proteins, and then stores the above values as the analytic values in the storage unit 350.

The time ($\tau_{off}$) of the duration of the interaction and the time ($\tau_{on}$) required for forming the following interaction between the first proteins and the second proteins obtained from the signal analyzing unit 340 may be analyzed to thereby obtain a series of data regarding the protein-protein interactions. The signal diagnosing unit 360 compares and analyzes the analytic values calculated in each condition, in which various cytoplasmic lysate are supplied to the substrate, and then performs the functions to deduct a biological and medical diagnosis for each cytoplasmic condition according to a predetermined diagnosis algorithm based on the results of comparing and analyzing.

According to the present invention, protein-protein interactions in the actual intracellular environment can be analyzed at a single molecule level.

In addition, according to the present invention, the degrees of effects of other proteins on specific protein-protein interactions can be analyzed when the other proteins are involved in the lysate corresponding to the normal intracellular environment.

While the invention has been shown and described with reference to certain exemplary embodiments thereof, it will be understood by those skilled in the art that various changes in form and details may be made therein without departing from the spirit and scope of the invention as defined by the appended claims.

What is claimed is:

1. An apparatus for analyzing protein interactions, comprising:
    a sample loading unit for loading a substrate comprising attached biomolecules which specifically bind to first markers tagged on first proteins, a wherein the first proteins are supplied to the substrate to induce binding of the biomolecules and the first markers, and cell lysate containing second markers-tagged second proteins that are supplied to the substrate;
    an optical excitation unit for generating a near-field having a first wavelength to a surface of the substrate loaded on the sample loading unit; and
    an optical measuring unit for detecting a change from the first wavelength to a second wavelength on the surface of the substrate according to the interactions between the first proteins and the second proteins in the cell lysate.

2. The apparatus of claim 1, wherein the optical measuring unit cumulatively measures a fluorescent signal having the second wavelength for a predetermined time period.

3. The apparatus of claim 1, wherein the optical measuring unit measures a fluorescent signal having the second wavelength in real time under the presence of the cell lysate.

4. The apparatus of claim 1, wherein the first marker and the second marker are fluorescent proteins having different wavelengths.

5. The apparatus of claim 1, further comprising a signal analyzing unit for analyzing the fluorescent signal having the second wavelength measured by the optical measuring unit through image processing.

6. An apparatus for analyzing protein interactions, comprising:
    a sample loading unit for loading a substrate comprising attached biomolecules a which specifically bind to first proteins, wherein the first proteins are supplied to the substrate and binds to the biomolecules, and cell lysate containing markers-tagged second proteins that are supplied to the substrate;
    an optical excitation unit for generating a near-field having a first wavelength to a surface of the substrate loaded on the sample loading unit; and
    an optical measuring unit for detecting a change from the first wavelength to a second wavelength on the surface of the substrate according to the interactions between the first proteins and the second proteins in the cell lysate.

7. The apparatus of claim 6, wherein the optical measuring unit cumulatively measures a fluorescent signal having the second wavelength for a predetermined time period.

8. The apparatus of claim 6, wherein the optical measuring unit measures a fluorescent signal having the second wavelength in real time under the presence of the cell lysate.

9. The apparatus of claim 6, further comprising a signal analyzing unit for analyzing the fluorescent signal having the second wavelength measured by the optical measuring unit through image processing.

* * * * *